United States Patent [19]

Ott

[11] Plant 4,595

[45] Sep. 23, 1980

[54] POINSETTIA

[76] Inventor: Cleveland Ott, 677 Grater Ave., Graterford, Pa. 19426

[21] Appl. No.: 2,466

[22] Filed: Jan. 10, 1979

[51] Int. Cl.[3] ..... A01H 5/00

[52] U.S. Cl. ..... Plt./86

[58] Field of Search ..... Plt./86

[56] References Cited

U.S. PATENT DOCUMENTS

P.P. 3,763 8/1975 Grotum ..... Plt./86

*Primary Examiner*—Robert E. Bagwill
*Assistant Examiner*—James R. Feyrer
*Attorney, Agent, or Firm*—Paul & Paul

[57] ABSTRACT

A new and distinct variety of poinsettia plant is a sport of Ott Poinsettia (U.S. Plant Pat. No. 4,310). The new variety is characterized by an upper layer of lobed bracts which stand out with more erectness and less droop than on the parent. The leaves also stand out with more erectness and less droop than on the parent.

ORIGIN OF THE VARIETY

The new variety of poinsettia plant was discovered by applicant as a sport in a bed of Ott poinsettias (U.S. Plant Pat. No. 4,310) in applicant's greenhouse in Graterford, Pa. The discovery was made in December 1977 but none of the new variety plant was sold, or offered for sale, until December 1978.

Asexual Reproduction of the Variety

Following applicant's discovery, applicant asexually reproduced the new and distinct variety of plant in his greenhouse by the rooting of cuttings of the new sport. The asexually reproduced poinsettia plants have uniformly new and distinct characteristics.

SUMMARY OF THE VARIETY

The new and distinct variety of poinsettia plant is characterized by the following features;

(1) The uppermost level of bracts includes from three to six bracts which are lobed. The stems of these lobed bracts project diagonally upwardly, from points on the dark green plant stem below the light green flower stem, through a layer of bracts which are not lobed. Thus, these lobed bracts, although carried by stems originating from the dark green plant stem below the light green flower stem, appear on the plant above the uppermost layer of non-lobed bracts which project outwardly from the light-green flower stem.

(2) The leaves projecting from the main plant stem are closely spaced.

(3) The bracts are wide and long.

(4) The bracts stand out; they do not droop.

(5) The bracts are dense; there is little space between bracts.

(6) The leaves stand out; they do not droop.

BRIEF DESCRIPTION OF THE DRAWING

The drawing comprises a photographic reproduction in color of the new and distinct poinsettia plant of this application.

DETAILED DESCRIPTION OF THE VARIETY

The new and distinct variety of poinsettia plant of this application was asexually reproduced from a sport of the parent (Ott U.S. Plant Pat. No. 4,310) which in turn is a sport of Annette Hegg Supreme (U.S. Plant Pat. No. 3,392), which in turn is a sport of Annette Hegg (U.S. Plant Pat. No. 2,962).

The bracts of the new variety of plant are the same color as the parent. The closest designations on the Royal Horticultural Society (RHS) color chart are near 44A to 45C. The closest designation on the Horticultural Color Chart (HCC) is Blood Red No. 820.

The uppermost level of bracts includes from three to six bracts which are lobed. The stems of these lobed bracts project diagonally upwardly, from locations on the dark-green plant stem below the light-green flow stem. These stems project through a layer of bracts which are not lobed and whose stems extend radially outwardly from the light-green flower stem. Thus, the lobed bracts, although carried by stems originating from the dark-green plant stem below the light-green flower stem, appear on the plant above the uppermost layer of non-lobed bracts.

The plant is shorter than the parent and more uniform in height.

The bracts are wide and long and closely spaced so that there is but little open space between bracts.

The bracts and the leaves stand more erect and do not droop as much as on the parent or as on any other preceding Annette Hegg variety.

The above comparisons are based on observations made of the new variety of plant and its parent grown side by side under the same environmental conditions.

1 Drawing Figure

What is claimed is:

1. A new and distinct variety of poinsettia plant, substantially as herein illustrated and described, characterized particularly as to novelty by having from three to six lobed bracts in the uppermost layer of bracts, the stems of these lobed bracts originating on the dark-green plant stem from locations below the light-green flower stem, the stems of these lobed bracts projecting diagonally upwardly through a layer of non-lobed bracts which project outwardly from the light-green flower stem, the bracts and the leaves standing out more erectly and not drooping as much as on the parent or other preceding Annette Hegg variety, the bracts being wide and long and densely spaced.

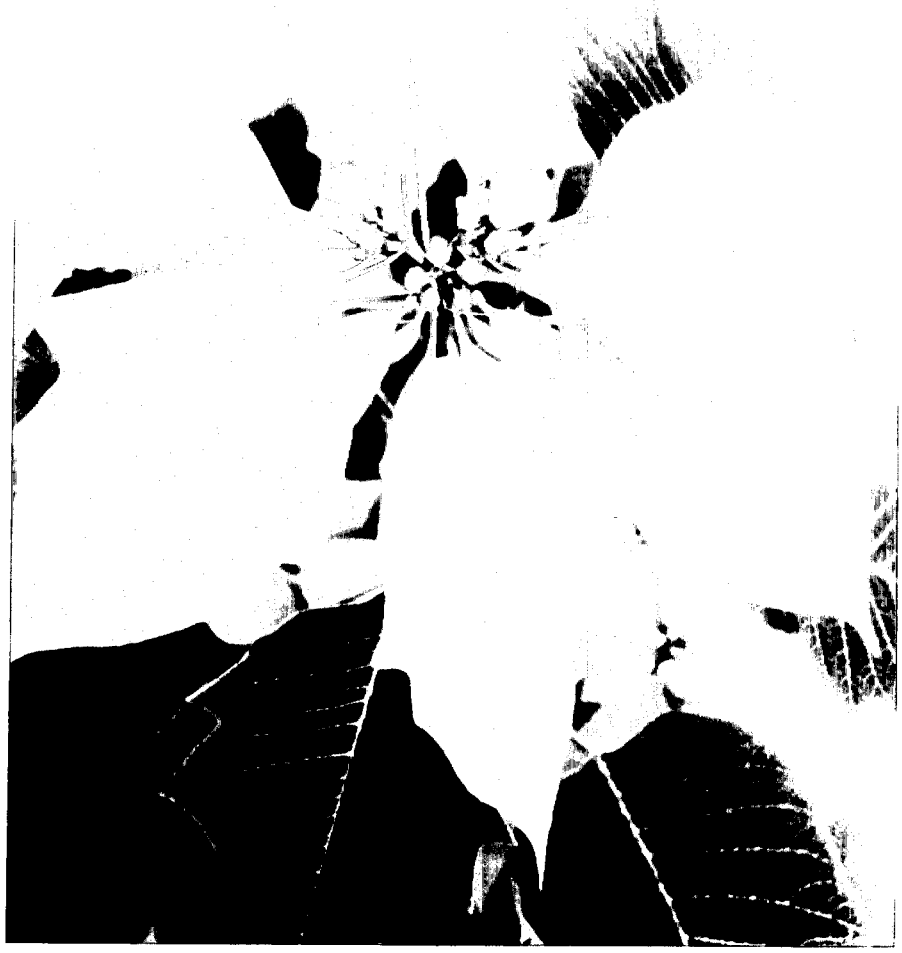

* * * * *